(12) United States Patent
Iversen et al.

(10) Patent No.: US 8,874,184 B1
(45) Date of Patent: Oct. 28, 2014

(54) MR CONDITIONAL NEEDLE AND SURFACE ELECTRODES

(71) Applicant: PMT Corporation, Chanhassen, MN (US)

(72) Inventors: Alfred A. Iversen, Wayzata, MN (US); Benjamin J. Osa, Edina, MN (US); Wade Fredrickson, Minnetonka, MN (US); Joseph Copley, Chaska, MN (US); Eric Caille, Minnetonka, MN (US)

(73) Assignee: PMT Corporation, Chanhassen, MN (US)

( * ) Notice: Subject to any disclaimer, the term of this patent is extended or adjusted under 35 U.S.C. 154(b) by 0 days.

(21) Appl. No.: 14/180,659

(22) Filed: Feb. 14, 2014

Related U.S. Application Data

(62) Division of application No. 12/799,240, filed on Apr. 21, 2010, now Pat. No. 8,682,409.

(60) Provisional application No. 61/214,237, filed on Apr. 21, 2009.

(51) Int. Cl.
*A61B 5/0492* (2006.01)
*A61B 5/0478* (2006.01)

(52) U.S. Cl.
CPC .................................. *A61B 5/0478* (2013.01)

USPC ........... 600/373; 600/372; 600/383; 600/395; 607/116

(58) Field of Classification Search
USPC .................. 600/372, 373, 383, 395; 607/116
See application file for complete search history.

(56) References Cited

U.S. PATENT DOCUMENTS

| | | | | |
|---|---|---|---|---|
| 4,537,198 | A * | 8/1985 | Corbett | 600/383 |
| 4,951,672 | A * | 8/1990 | Buchwald et al. | 600/421 |
| 5,445,162 | A * | 8/1995 | Ives | 600/544 |
| 6,032,063 | A * | 2/2000 | Hoar et al. | 600/372 |
| 6,115,623 | A * | 9/2000 | McFee | 600/372 |
| 6,415,169 | B1 * | 7/2002 | Kornrumpf et al. | 600/382 |
| 6,571,123 | B2 * | 5/2003 | Ives et al. | 600/544 |
| 6,708,051 | B1 * | 3/2004 | Durousseau | 600/383 |
| 7,440,789 | B2 * | 10/2008 | Hannula et al. | 600/383 |
| 7,996,056 | B2 * | 8/2011 | Rowlandson et al. | 600/386 |
| 2005/0251004 | A1 * | 11/2005 | Istvan et al. | 600/395 |
| 2006/0161058 | A1 * | 7/2006 | Ives et al. | 600/373 |

* cited by examiner

*Primary Examiner* — Lee S Cohen
(74) *Attorney, Agent, or Firm* — Eggink & Eggink; Anthony G. Eggink; Katrina M. Eggink

(57) ABSTRACT

MR conditional needle and surface electrode assemblies. The surface electrode utilizes a disc or cone-shaped structure with a bore with a concave bottom surface for receiving a conductive gel and an insulated wire with a connector for an EEG. The needle electrode assembly utilizes a cylindrical-shaped structure and is constructed of an MR conditional material having a needle and an insulated lead wire structure with a connector for an EEG.

20 Claims, 2 Drawing Sheets

MR CONDITIONAL NEEDLE AND SURFACE ELECTRODES

This application is a Division of U.S. patent application Ser. No. 12/799,240, filed on Apr. 21, 2010, now U.S. Pat. No. 8,682,409 issued on Mar. 25, 2014 and claims the benefit of U.S. Provisional Patent Application Ser. No. 61/214,237, filed on Apr. 21, 2009.

BACKGROUND OF THE INVENTION

The present invention relates generally to MR conditional electrode assemblies. Particularly, the present invention relates to needle and surface electrodes used in connection with Magnetic Resonance Imaging (MRI). More particularly, the invention relates to MR conditional needle and surface electrodes for use intraoperatively in operating room MRI suites and for long-term electroencephalogram (EEG) monitoring in Intensive Care Units (ICU's).

The terminology used for implants and devices in the MRI environment has evolved. For example, the term MRI or MR Compatible was used to describe a device that demonstrated neither a significant affect on the quality of the diagnostic information nor having its operations affected by the MR system. Currently, the MR task group of the American Society for Testing and Materials (ASTM) International developed a new set of terms. The electrodes of the present invention will thus be referred to as MR Conditional. The latter meaning a device that has demonstrated to pose no known hazards in a specified MRI environment with specified conditions of use.

Surface electrodes are used in the intensive care units (ICU) for patient monitoring. Needle electrodes may be used, for example, for patients that have been sedated prior to being in the ICU.

Regarding the prior art, needle and surface electrodes are commonly composed of stainless steel needles and recording discs or cones and the associated wires are typically composed of copper, tin, or carbon fiber leads. Stainless steel, tin, and copper are not MR conditional. The prior art does not teach or suggest a suitable MR conditional electrode structure. For example, Prior Art U.S. Pat. No. 5,445,162 discloses both sphenoidal "wire" electrodes made of silver and surface electrodes with a surface of gold or silver. However, the '162 patent does not disclose needle and surface electrodes constructed of materials comprising titanium, carbon fiber, carbon graphite, carbon impregnated polymers or ceramics.

One disadvantage of current needle and surface electrodes is that they must be removed before Magnetic Resonance Imaging (MRI) scans because the existing needles are not MR conditional. This disadvantage adds cost, considerable amount of time delays and potential inconsistencies recording pre versus post MR scan (due to the amount of time required to remove and then reposition the electrodes to the positions prior to the MR scan). The electrodes of the invention are constructed of lead-wires, needles and recording disc structures which are constructed of non-magnetic materials.

It is advantageous for caretakers to have electrodes that do not require the removal from the patient for MRI scans and then reapplied when the patient returns. It may, for example, require up to three hours to properly reposition the surface and needle electrodes on a patient.

SUMMARY OF THE INVENTION

Subdermal needle electrodes are disposable devices used to detect electrophysiological signals or to provide electrical stimulation subcutaneously. Surface electrodes are disposable or reusable non-sterile devices used to detect electrophysiological signals or to provide electrical stimulation subcutaneously. The electrodes are the interface medium between the diagnostic or monitoring equipment and the patient.

Subdermal needle electrodes are invasive, positioned subcutaneously, and are used under the supervision of a licensed physician. Surface electrodes are non-invasive and are placed on the patient by medical staff.

Subdermal needle and surface electrodes are for use with recording, monitoring and stimulation/recording equipment for the recording of biopotential signals including electroencephalograph (EEG), electromyography (EMG) and nerve potential signals and for stimulation during the intraoperative diagnosis of acute dysfunction in corticospinal axonal conduction. Used in clinical electro-diagnostic studies or intraoperative monitoring which may include electroencephalography (EEG), electromyography (EMG) or evoked potentials recording and electrical stimulation.

The surface electrode of the invention is comprised of a generally cylindrical disc or cone structure with a concave bottom section and with a small through-hole or bore extending from the top to the concave bottom which allows injection of conductive gel or paste into the concave section of the disc to provide for better EEG recordings. Electrically connected to the disc or cone is a lead wire having a "touch-proof" safety connector on its terminal end. The surface electrode is typically taped into place on the patient. The safety connector is constructed for connection to recording, stimulating or monitoring equipment.

The connector is specifically designed so that it cannot be plugged into an AC power outlet. If desired, a quick disconnect along the lead wire length may be used for quick disconnection of the electrode from the recording equipment. The electrodes may be grouped together for several recording channels with one quick disconnection to speed up the process of disconnection several electrodes at once. Leads for the electrodes are preferably multicolored to properly differentiate between different contacts quickly by medical personnel. Electrodes may be numbered or lettered at the recording side and the EEG plug side.

It is a benefit of the present invention to provide electrodes that are MR conditional and do not need to be removed from a patient for MRI scans, for example.

These and other benefits and advantages of this invention will become clear from the following description by reference to the drawings.

DESCRIPTION OF THE PREFERRED EMBODIMENTS

Subdermal needle electrodes are disposable devices used to detect electrophysiological signals or to provide electrical stimulation subcutaneously. Surface electrodes are disposable or reusable non-sterile devices used to detect electrophysiological signals or to provide electrical stimulation subcutaneously. The electrodes are the interface medium between the diagnostic or monitoring equipment and the patient.

Figure 1:
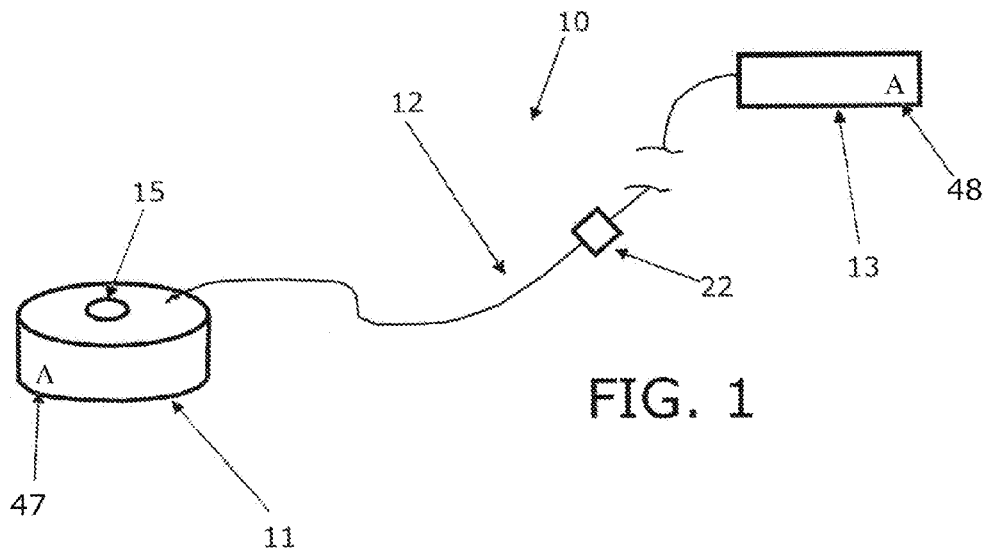
FIG. 1 is a perspective view of the surface electrode assembly of the invention.
Figure 2:
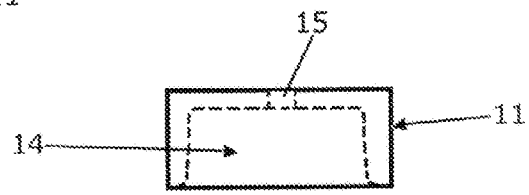
FIG. 2 is a sectional view of the disc structure of FIG. 1.

Referring to FIGS. 1 and 2, the surface electrode assembly 10 is shown comprised of a generally round shaped disc 11 or cone with a concave bottom section or cavity 14 with a small through hole 15 in the top which allows injection of conductive gel or paste into the concave bottom section to provide for better EEG recordings. The generally round shaped disc or cone 11 is located on one end of the surface electrode assembly 10 and is electrically connected to a lead wire 12 and a "touch-proof" safety connector or quick disconnect 22 located on the other end. The surface electrode is typically taped into place. The safety connector is connected to recording or monitoring equipment, for example, EEG plug 13. The electrode disc or cone 11 is preferably constructed of an MR conditional titanium, silver, nitinol (a nickel titanium alloy), a plastic substrate with silver-silver chloride, carbon fiber or carbon graphite, carbon impregnated plastic or ceramic composites, all known in the art to be rigid materials.

Figure 3:
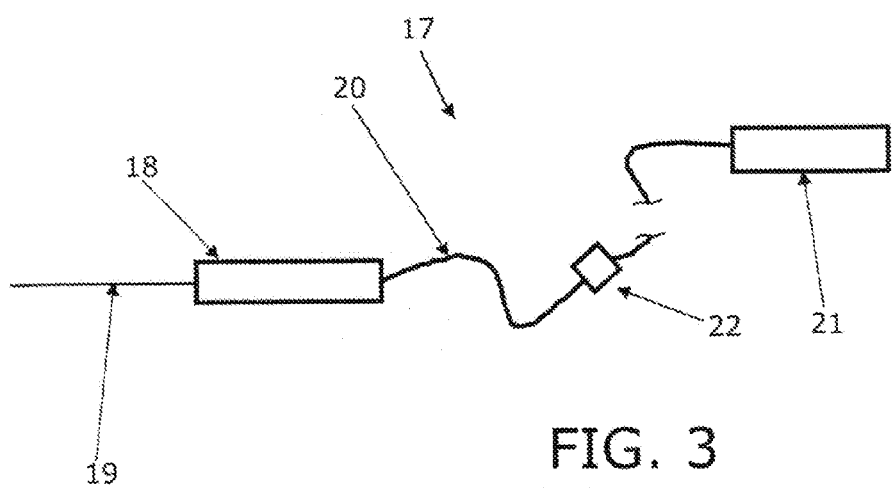
FIG. 3 is a plan view of the needle electrode assembly of the invention.

As shown in FIG. 3, the subdermal needle electrode assembly 17 is comprised of a small gauge titanium needle 19 connected to body 18 on one end and electrically connected to a lead wire 20 and a "touch-proof" safety connector 22 on the other end. The needle is inserted subdermally by a licensed physician or technologist under the supervision of a physician. The needle 19 is shown extending from the periphery of the cylindrical body 18 which may be formed of a rigid MR conditional plastic resin composition.

Figure 4:
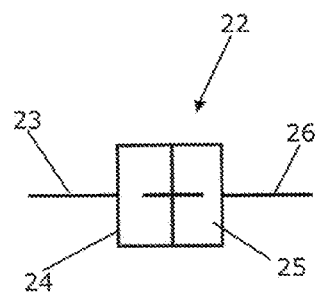
FIG. 4 is a plan view showing a quick device disconnect incorporated into a lead wire.
Figure 5:
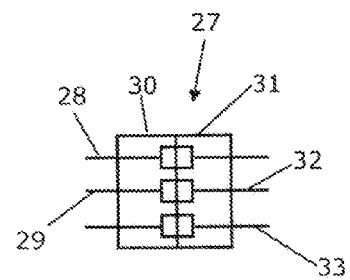
FIG. 5 is a schematic of a quick disconnection device which may be utilized with multiple lead wires.
Figure 7:
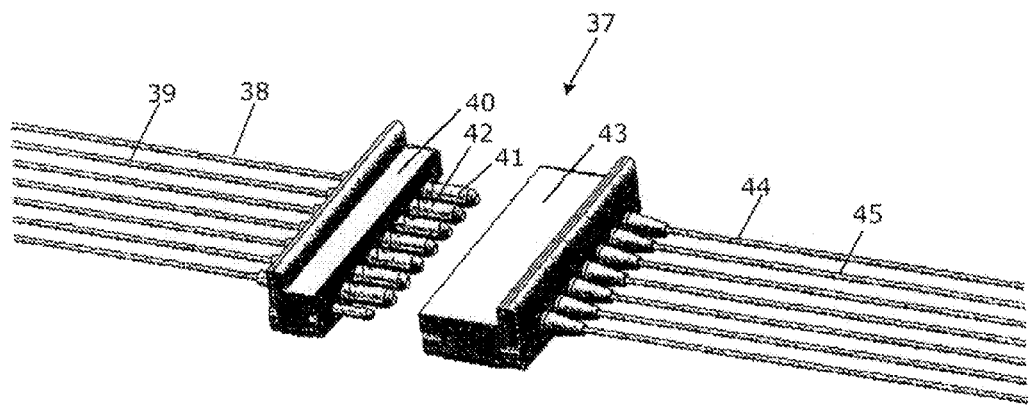
FIG. 7 is a perspective view of a quick disconnect device for a plurality of lead wires.

The connector plug at the terminal end of the lead wire is specifically designed so that it cannot be plugged into an AC power outlet. If desired and as shown in FIGS. 4, 5 and 7, a quick disconnect plug 22, 27, 37 (respectively) along the lead wire length may be used for quick disconnection of the electrode from the recording equipment. FIG. 4 shows lead wire 23, being joined to lead wire 26 by quick disconnect plug 22 having mating body parts 24 and 25. FIG. 5 shows lead wires 28, 29 being joined to lead wires 32, 33 by quick disconnect plug 27 having mating body parts 30, 31. The electrodes may be grouped together for several recording channels with one quick disconnection to speed up the process of disconnection of several electrodes at once, as shown with the devices of FIGS. 5 and 7. Leads for the electrodes are preferably multi-colored to properly differentiate between different contacts quickly by medical personnel. Electrodes may be numbered or lettered at the recording side and the EEG plug side, as shown in FIG. 1 by markings 47 and 48, respectively. As shown, for example, the letter A is marked on electrode body structure 11 and on its corresponding EEG plug 13.

The lead wire is bonded to the surface electrode disc or cone, or the subdermal needle using conductive epoxy, welding, crimping, soldering, insert molded in place or other known means. The device is potted by over molding, insert molding, or potting epoxy adhesive or UV cure adhesive. The EEG plug is bonded to the lead wire using soldering, welding, crimping or conductive epoxy. The length of the lead wire may vary based upon user preference, however the standard length is approximately five feet. The lead wire is preferably constructed of MRI-conditional wire made with nitinol (a nickel titanium alloy), silver, platinum, titanium, titanium alloy, carbon-fiber, braided carbon-fiber, Nichrome (a nickel chrome alloy) or Tinsel (low voltage electrical wire).

Figure 6:
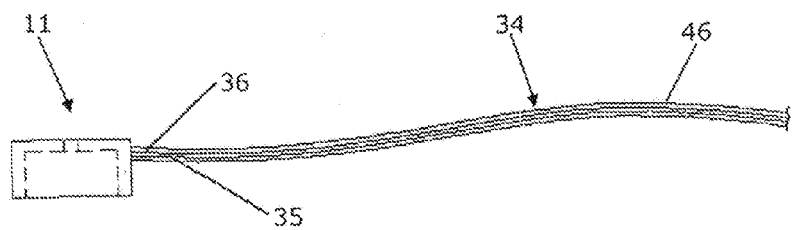
FIG. 6 is a lateral sectional view of a lead wire structure used in the assembly of the invention.

FIG. 6 shows disc 11 having a reinforced lead wire structure 34 extending therefrom and having a reinforcement wire 36 extending within the structure in a generally parallel arrangement along with signal carrying lead wire 35. The material and size of lead wires may not provide sufficient strength and durability. The addition of the reinforcement lead(s) provides increased strength and durability of the lead wire structure. Insulated covering 46 is shown around wires 35 and 36.

FIG. 7 shows a quick disconnect device 37 having cooperating male and female connector portions 40 and 43, respectively, and which permit a plurality of leads 38, 39, 44, 45 to be connected so as to provide a quicker and easier way to use disconnect and reconnection devices. Connectors 41 and 42 of male connector portion 40 are shown for engagement with female connector portion 43.

The needle of FIG. 3 has a diameter of approximately 0.015 inches, and which may vary by +/−0.010 inches. The diameter of the surface electrode is approximately ⅜ inches but may vary based upon user preference. The needle is preferably constructed of a MR conditional material including titanium, silver and nitinol.

In summary, the MR conditional electrode assemblies of the invention include needle and surface electrodes constructed of MR conditional materials set forth above. The MR conditional materials may include combinations of such materials as well as coatings comprised of these MR conditional materials.

As many changes are possible to the MR conditional needle and surface electrodes of this invention utilizing the teachings thereof, the descriptions above and the accompanying drawings should be interpreted in the illustrative and not in the limited sense.

That which is claimed is:

1. An MR conditional needle electrode assembly comprising:
   a) a hub structure having a periphery and formed of an MR conditional material;
   b) a needle extending outwardly from said periphery of said hub structure;
   c) an insulated flexible lead wire structure containing a signal carrying wire communicating with said needle, said insulated flexible lead wire structure extending from said hub structure and having a terminal end;
   d) a plug connected to said terminal end of said insulated flexible lead wire structure for connection to an EEG assembly; and
   e) a quick disconnect device incorporated in said insulated flexible lead wire structure and positioned between said hub structure and said plug, said quick disconnect device constructed to receive a plurality of said lead wire structures in an aligned configuration so that said lead wire structures remain in a parallel configuration with respect to each other into and extending from said quick disconnect device.

2. The MR conditional needle electrode assembly of claim 1, wherein said hub structure is constructed of a MR conditional plastic resin composition.

3. The MR conditional needle electrode assembly of claim 1, wherein said needle is constructed of a material selected from the group of materials consisting of titanium, silver and nickel titanium alloy.

4. The MR conditional needle electrode assembly of claim 1, wherein said lead wire structure has a reinforcement wire therein.

5. The MR conditional needle electrode assembly of claim 1, wherein said hub structure and said plug are marked with a marking selected from the group of markings consisting of a number, a letter and a number/letter combination.

6. The MR conditional needle electrode of claim 5 wherein said marking of said hub structure corresponds to the marking of said plug.

7. An MR conditional needle electrode assembly comprising:
   a) a plurality of generally cylindrical, rigid electrode body structures each having a lateral periphery and constructed of an MR conditional material, each said electrode body structure having a needle structure extending outwardly therefrom, each said electrode body having a marking;
   b) an insulated flexible lead wire structure having a terminal end and extending from each said generally cylindrical electrode body structure, each said flexible lead wire structure including a signal carrying wire electrically communicating with said needle structure and a reinforcement wire disposed in a generally parallel arrangement within each said insulated flexible lead wire structure, each said lead wire structure having a color;
   c) a plug connected to said terminal end of said insulated flexible lead wire structure, each said plug being constructed for connection to an EEG assembly and being marked with a marking corresponding to said marking on said electrode body structure; and
   d) a quick disconnect device constructed to receive a plurality of lead wire structures and interposed between each said generally cylindrical body structure and said plug at said terminal end of each said insulated flexible lead wire structure, said quick disconnect device being constructed to receive said plurality of lead wire structures in an aligned configuration so that at said quick disconnect device each said lead wire structure remains in an aligned, parallel configuration with respect to each other and wherein said color of each said leadwire structure visually aids in the connection of said quick disconnect device.

8. The MR conditional needle electrode assembly of claim 7, wherein said MR conditional material of said generally cylindrical body structure is a plastic resin composition.

9. The MR conditional needle electrode assembly of claim 7, wherein said signal carrying wire of said insulated flexible lead wire structure is constructed of an MR conditional material selected from the group of materials consisting of a nickel titanium alloy, silver, platinum, titanium, titanium alloy, carbon fiber, braided carbon-fiber, or a nickel chrome alloy.

10. The MR conditional needle electrode assembly of claim 7, wherein said needle structure is constructed of a material selected from the group of materials consisting of titanium, silver and a nickel titanium alloy.

11. The MR conditional needle electrode assembly of claim 7, wherein said marking is selected from the group of markings consisting of a number, a letter and a number/letter combination.

12. An MR conditional needle electrode assembly comprising:
   a) an electrode body structure formed of an MR conditional material and having a needle structure extending outwardly therefrom;
   b) an insulated flexible lead wire structure extending from said electrode body structure and having a terminal end, said insulated flexible lead wire structure having a signal carrying wire in electrical communication with said needle structure and further having a reinforcement wire disposed in a generally parallel arrangement with said signal carrying wire and within said insulated flexible lead wire structure;
   c) a plug connected to said terminal end of said insulated flexible lead wire structure for connection to an EEG assembly; and
   d) a quick disconnect device incorporated in said insulated flexible lead wire structure and positioned between said electrode body structure and said plug, said quick disconnect device constructed to receive a plurality of said lead wire structures in an aligned configuration so that said lead wire structures remain in a parallel configuration with respect to each other into and extending from said quick disconnect device.

13. The MR conditional needle electrode assembly of claim 12, wherein said electrode body structure has a generally cylindrical configuration having a periphery and wherein said needle structure extends from said periphery.

14. The MR conditional needle electrode assembly of claim 12, wherein said signal carrying wire of said insulated flexible lead wire structure is constructed of an MR conditional material selected from the group of materials consisting of a nickel titanium alloy, silver, platinum, titanium, titanium alloy, carbon fiber, braided carbon-fiber, or a nickel chrome alloy.

15. The MR conditional needle electrode assembly of claim 12, wherein a plurality of needle electrode assemblies are provided, each having a lead wire structure whereby a plurality of lead wire structures are provided and wherein said plurality of lead wire structures are multicolored.

16. The MR conditional needle electrode of claim 15, said quick disconnect device being constructed to receive a plurality of multicolored lead wire structures in a parallel and aligned configuration into and extending from said quick disconnect device.

17. The MR conditional needle electrode assembly of claim 12, wherein said electrode body structure and said plug are marked with a marking selected from the group of markings consisting of a number, a letter and a number/letter combination.

18. The MR conditional needle electrode of claim 17, wherein said marking of said electrode body structure corresponds to the marking of said plug.

19. The MR conditional needle electrode assembly of claim 12, wherein said needle structure is constructed of a material selected from the group of materials consisting of titanium, silver and a nickel titanium alloy.

20. The MR conditional needle electrode assembly of claim 12, wherein said electrode body structure is constructed of a MR conditional plastic resin composition.

\* \* \* \* \*